United States Patent
Bergren et al.

(10) Patent No.: US 10,082,387 B2
(45) Date of Patent: Sep. 25, 2018

(54) FLUORESCENT LIQUID PENETRANTS AND METHODS OF NONDESTRUCTIVE TESTING

(71) Applicant: UbiQD, LLC, Los Alamos, NM (US)

(72) Inventors: Matthew R. Bergren, Los Alamos, NM (US); Hunter McDaniel, Los Alamos, NM (US)

(73) Assignee: UbiQD, Inc., Los Alamos, NM (US)

( * ) Notice: Subject to any disclaimer, the term of this patent is extended or adjusted under 35 U.S.C. 154(b) by 0 days.

(21) Appl. No.: 15/455,111

(22) Filed: Mar. 9, 2017

(65) Prior Publication Data
US 2017/0261313 A1    Sep. 14, 2017

Related U.S. Application Data

(60) Provisional application No. 62/305,707, filed on Mar. 9, 2016.

(51) Int. Cl.
| | |
|---|---|
| *G01N 21/25* | (2006.01) |
| *G01B 11/22* | (2006.01) |
| *G01N 21/64* | (2006.01) |
| *G01N 33/20* | (2006.01) |
| *G01N 33/00* | (2006.01) |

(52) U.S. Cl.
CPC ........... *G01B 11/22* (2013.01); *G01N 21/643* (2013.01); *G01N 33/20* (2013.01); *G01N 2021/6439* (2013.01); *G01N 2033/0078* (2013.01); *G01N 2201/062* (2013.01); *G01N 2201/06113* (2013.01)

(58) Field of Classification Search
CPC ................. G01N 21/643; G01N 33/20; G01N 2021/6439; G01N 2033/0078; G01N 2201/06113; G01N 2201/062; G01B 11/22

USPC .......................................................... 356/417
See application file for complete search history.

(56) References Cited

U.S. PATENT DOCUMENTS

| | | | | |
|---|---|---|---|---|
| 3,708,665 A * | 1/1973 | Prine | ...................... | G01N 21/91 250/330 |
| 3,735,131 A * | 5/1973 | Sherwin | ................. | G01N 21/91 250/302 |
| 3,877,819 A * | 4/1975 | Haas | ...................... | G01N 21/72 356/417 |

(Continued)

OTHER PUBLICATIONS

Valeur et al. ("Molecular Fluorescence: Principles and Applications", John Wiley & Sons, Mar. 27, 2013).*

*Primary Examiner* — Hina F Ayub
(74) *Attorney, Agent, or Firm* — John A. Fortkort; Fortkort & Houston PC

(57) ABSTRACT

A fluorescent liquid penetrant is provided which includes a liquid medium having a plurality of fluorophores disposed therein. Upon excitation with a suitable light source, the penetrant exhibits a quantum yield greater than 40% (or in some embodiments, greater than 90%). In some embodiments, the fluorophore is a low-toxicity quantum dot. In some embodiments, the fluorophore has significantly reduced self-absorption, which allows for surface discontinuity depth measurement. Also disclosed are apparatuses for using these fluorescent liquid penetrants for non-destructive testing purposes. In some embodiments, these tests include measuring the depth of a discontinuity by analyzing photoluminescence intensity and/or photoluminescence peak position shift.

21 Claims, 7 Drawing Sheets

(56) References Cited

U.S. PATENT DOCUMENTS

| | | | | |
|---|---|---|---|---|
| 4,968,892 | A * | 11/1990 | McAtee | G01N 21/91 250/302 |
| 5,009,102 | A * | 4/1991 | Afromowitz | G01N 21/4133 73/590 |
| 5,795,712 | A * | 8/1998 | Beriozkina | G01N 21/91 252/408.1 |
| 2002/0189757 | A1* | 12/2002 | Denton | G01K 11/12 156/345.27 |
| 2008/0220593 | A1* | 9/2008 | Pickett | B82Y 30/00 438/478 |
| 2009/0004471 | A1* | 1/2009 | Amthor | A61B 5/04001 428/375 |
| 2011/0253198 | A1* | 10/2011 | Patrick | B82Y 20/00 136/247 |
| 2012/0214253 | A1* | 8/2012 | Butlin | C07D 487/18 436/172 |
| 2012/0233111 | A1* | 9/2012 | Kush | G01N 21/91 706/52 |
| 2013/0020507 | A1* | 1/2013 | Zhang | C07F 5/022 250/459.1 |
| 2014/0364707 | A1* | 12/2014 | Kintz | A61B 5/1459 600/310 |
| 2015/0297086 | A1* | 10/2015 | Hong | G01N 21/6428 600/431 |
| 2017/0218264 | A1* | 8/2017 | Klimov | C09K 8/80 |
| 2017/0227515 | A1* | 8/2017 | Euler | G01N 33/227 |

\* cited by examiner

FLUORESCENT LIQUID PENETRANTS AND METHODS OF NONDESTRUCTIVE TESTING

CROSS-REFERENCE TO RELATED APPLICATIONS

This application claims the benefit of priority from U.S. provisional application No. 62/305,707, filed Mar. 9, 2016, having the same title and the same inventor, and which is incorporated herein by reference in its entirety.

FIELD OF THE DISCLOSURE

The present disclosure relates generally to photoluminescent materials, and more specifically to fluorescent liquid penetrant compositions containing photoluminescent materials, such as quantum dots, and to apparatuses for using the same for non-destructive testing and dimensional analysis purposes.

BACKGROUND OF THE DISCLOSURE

Non-destructive testing (NDT) is a widely-used method for determining surface defects in manufactured equipment and welding applications. One NDT technique utilizes a red dye penetrant which enters into small surface flaws in order to make them more visible. This testing method, called liquid penetrant examination (LPE), is a popular technique since it easily reveals previously hard-to-see cracks, corrosion pits, or other surface damage in the manufactured parts. For enhanced contrast and detection of smaller surface flaws, fluorescent penetrants that emit a green glow when illuminated with ultraviolet (UV) light are frequently used.

LPE is particularly useful in examining machined parts on weaponry, where early identification of surface flaws may help prevent a catastrophic failure due to the high pressures and high temperatures that can exist inside the weapon. LPE is also commonly used to detect flaws in welding, where small fractures in welds can result in failure of the weld. NDT is preferred over other quality inspection techniques (which may require damaging the part), since the tested material remains useable after NDT (if no defects were detected).

Photoluminescence (PL) is the emission of light (electromagnetic radiation, photons) after the absorption of light. It is one form of luminescence (light emission) and is initiated by photoexcitation (excitation by photons). Following photon excitation, various charge relaxation processes may occur in which other photons with a lower energy, compared to the excitation source, are re-radiated on some time scale. The energy difference between the absorbed photons and the emitted photons (also known as Stokes shift) can vary widely across materials from nearly zero to 1 eV or more.

SUMMARY OF THE DISCLOSURE

Figure 1:
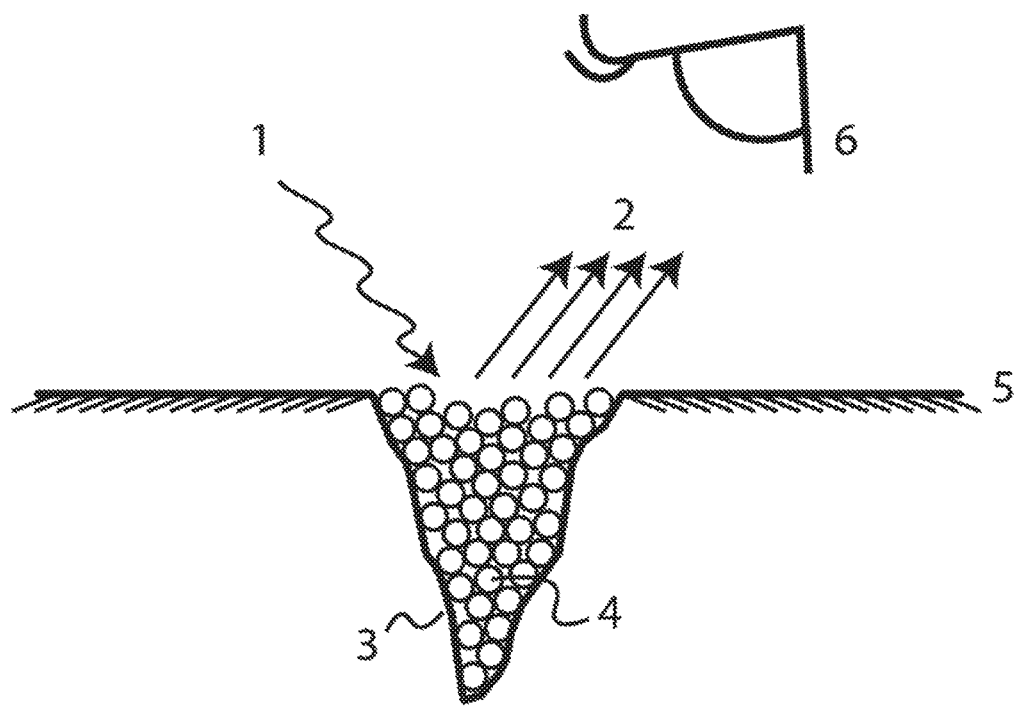
FIG. 1 is a schematic illustration of a quantum dot (QD) fluorescent liquid penetrant applied to a surface discontinuity wherein an observer identifies the surface discontinuity from the fluorescence of the liquid penetrant when excited by a light source.

In one aspect, a fluorescent liquid penetrant is provided which comprises (a) a liquid medium; and (b) a plurality of quantum dots disposed in said medium which, upon excitation with a light source, exhibit a quantum yield greater than 40%, and low self-absorption such that the photoluminescence is absorbed by less than 50% across the integrated spectrum by said fluorescent liquid penetrant over distances of 100 nm to 10 cm.

In another aspect, a fluorescent liquid penetrant is provided which comprises (a) a liquid medium; and (b) a plurality of fluorophores disposed in said medium which, upon excitation with a light source, exhibit a quantum yield greater than 40%, and low self-absorption such that the photoluminescence is absorbed by less than 50% across the integrated spectrum by said fluorescent liquid penetrant over distances of 100 nm to 10 cm.

In another aspect, and in combination with a fluorescent liquid penetrant, an optical apparatus for analyzing the photoluminescent properties of said fluorescent liquid penetrant is provided. The optical apparatus comprises (a) a time-varying light source which excites said fluorescent liquid penetrant, thereby causing said fluorescent liquid penetrant to emit an emission spectrum having photoluminescent properties characterized by the depth of the surface discontinuity; (b) at least one photodetector; and (c) an electronics module which determines the photoluminescence properties of said fluorescent liquid penetrant.

In a further aspect, a method is provided for quantifying the depth of surface discontinuities wherein a fluorescent liquid penetrant has penetrated into said surface discontinuity. The method comprises (a) irradiating the fluorescent liquid penetrant with a time-varying light source; (b) ascertaining the photoluminescent spectrum of the irradiated fluorescent liquid penetrant with at least one photodetector; and (c) quantifying the depth of the surface discontinuity wherein the fluorescent liquid penetrant has penetrated into said surface discontinuities.

In still another aspect, a method is provided for quantifying the depth of surface discontinuities. The method comprises (a) a first liquid penetrant for first identifying said surface discontinuities; (b) removal of said first liquid penetrant; (c) a second liquid penetrant that fluoresces when irradiated with a time-varying light source; (d) ascertaining the photoluminescent spectrum of the irradiated fluorescent liquid penetrant with at least one photodetector; and (e) quantifying the depth of the surface discontinuity wherein the fluorescent liquid penetrant has penetrated into said surface discontinuities.

DETAILED DESCRIPTION

1. Background

Current fluorescent penetrant examination methods utilize a multi-step procedure that includes multiple cleaning, baking and dwell steps. These methods also typically require the application of two products, namely, a fluorescent penetrant (which enters into the surface flaws) and a developer (which draws out the penetrant for clearer identification). While current fluorescent penetrant technology is the preferred non-destructive testing (NDT) method, there are several draw backs to this method. First of all, current LPE methods are multi-step procedures that can be time intensive, especially when examining multiple parts. Secondly, many of the current fluorescent dyes used in these methods have absorption onsets that overlap the emission spectrum. This causes a problem called self-absorption, a process in which photons emitted by dye molecules are reabsorbed by neighboring molecules. This process may occur multiple times, and each subsequent self-absorption event will increase the probability of non-radiative relaxation occurring instead of photon emission. This ultimately results in weaker luminescence, which may adversely affect the ability to observe the surface flaws or to quantify the depth of cracks.

The brightness of the dye's luminescence plays a large role in the detectability of small surface flaws, since the visibility of such defects decreases as the dimensions of the defect become smaller. Luminescence is especially important when a fluorescent penetrant is used in applications involving the inspection of critical components of systems in which malfunctions may result in injury or death.

For example, fluorescent penetrants are frequently used to inspect the bore evacuator holes for gun tubes. The bore evacuator holes are very small and, if defective, run the risk of rendering the bore evacuators inoperable. This, in turn, may leave residual propellant gas in the gun tube, which is dangerous to its operators. In particular, such residual gas may enter a closed-fighting compartment, making it difficult to breathe or see. Such residual gas may also ignite ready ammunition in the compartment. See D. E. Carlucci and S. S. Jacobson, "Ballistics: Theory and Design of Guns and Ammunition," Boca Raton, Fla.: CRC Press, 2008. Self-absorption also eliminates the possibility of discerning any depth information of the surface flaw since the PL intensity won't necessarily scale with depth.

Colloidal semiconductor nanocrystals, or quantum dots (QDs), are vanishingly small pieces of semiconductor material that are typically less than 20 nm in diameter. Owing to their small size, these materials have several advantageous properties that include size-tunable photoluminescence (PL) emission over a wide-range of colors, a strong and broadband absorption as well as remarkably high PL efficiency. Changing the size of the QDs is also relatively straightforward due to the solution processing techniques used to synthesize these materials. The ability to tune the QD size, and therefore the absorption/emission spectra, allows for flexible fluorescence across the full color spectrum without needing to modify the material composition.

As the QD size increases, the absorption onset and photoluminescence (PL) spectrum shifts to redder wavelengths (lower photon energies). Conversely, as QD sizes decrease, the absorption and PL shift towards bluer wavelengths (higher photon energies). The size tunability of colloidal QDs would be beneficial for LPE if used as the fluorescent dye. In particular, this feature allows different colored penetrants to be produced so that the end user can choose a color that will provide good visual contrast to the color of the part being tested.

It is typically important for the fluorescent penetrant used in LPE to have a strong contrast from the sample being tested, since this allows for facile identification of surface discontinuities. The broadband absorption of colloidal QDs is also ideal for LPE, since it allows less material to be used to produce a bright indicator under a variety of excitation sources. Such broadband absorption may also allow these materials to be used without a developer, which would further reduce testing time and costs. The very small size of the nanocrystals also means they can easily be dissolved into, and deposited from, liquid solvents (e.g. oils, ethanol, toluene, water). Using solution synthesis techniques to fabricate QDs is typically a more cost-effective and scalable approach as compared to alternative synthesis methods such as plasma synthesis or top-down etching.

Figure 2:
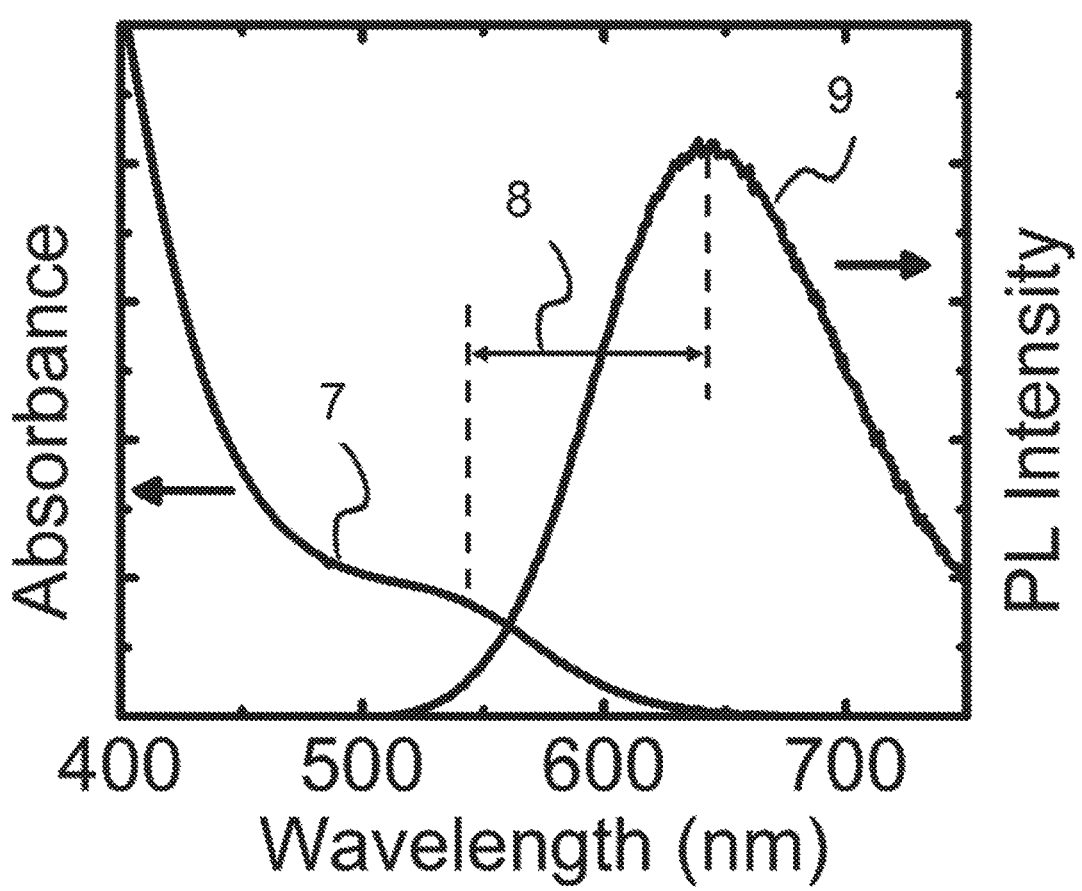
FIG. 2 is a graph of a typical absorption and photoluminescence spectra for an exemplary CuInZnS QDs. These QDs are substantially free of toxic elements and are believed to be non-carcinogenic. These QDs also have low self-absorption due to a large gap between absorption and photoluminescence (Stokes shift).

At present, the best performing I-III-VI QDs are composed of $CuInS_2$ (CIS), which have the potential to be disruptive in the emerging QD industry owing to their lower manufacturing costs, lower toxicity, and high photoluminescence quantum yield. $CuInS_2$ beats the typical QD material, CdSe, on the critical metrics of toxicity and cost and photoluminescence quantum yields (>95%). On other performance metrics, $CuInS_2$ QDs are favorable as well. For example, CIS QDs have stronger absorption than CdSe QDs and also have a large Stokes shift (~450 meV; see FIG. 2), which limits self-absorption in the material. By contrast, CdSe QDs have Stokes shifts of less than 100 meV.

A third problem with most fluorescent dyes is their narrow absorption range, which limits the possible wavelengths of light used to excite the dye. Therefore, if different fluorescent liquid penetrant colors are needed in order to provide contrast with the tested part, different excitation sources would be needed for each color of dye.

The overall cost of the current LPE technology could be lowered by reducing the number of steps in the testing process. Additionally, it would be advantageous to not only detect surface defects in manufactured parts, but also quantify their depth by analyzing the intensity of light emitted. Although quantum dots have been proposed as a solution to the limitations of fluorescent dye-based LPE (K. Daneshvar and B. Dogan, "Application of quantum dots as a fluorescent-penetrant for weld crack detection," MATERIALS AT HIGH TEMPERATURES 2010, 27, 179), no products have been developed to date, and the self-absorption and toxicity problems were not recognized.

Nanocrystal quantum dots of the I-III-VI class of semiconductors, such as $CuInS_2$, are of growing interest for applications in optoelectronic devices such as solar photovoltaics (see, e.g., PVs, Stolle, C. J.; Harvey, T. B.; Korgel, B. A. Curr. Opin. Chem. Eng. 2013, 2, 160) and light-emitting diodes (see, e.g., Tan, Z.; Zhang, Y.; Xie, C.; Su, H.; Liu, J.; Zhang, C.; Dellas, N.; Mohney, S. E.; Wang, Y.; Wang, J.; Xu, J. Advanced Materials 2011, 23, 3553). These quantum dots exhibit strong optical absorption and stable efficient photoluminescence that can be tuned from the visible to the near-infrared (see, e.g., Zhong, H.; Bai, Z.; Zou, B. J. Phys. Chem. Lett. 2012, 3, 3167) through composition and quantum size effects. In fact, Grätzel cells sensitized by specifically engineered I-III-VI quantum dots have recently been shown to offer excellent stability and certified power conversion efficiencies of >5% (see McDaniel, H.; Fuke, N.; Makarov, N. S.; Pietryga, J. M.; Klimov, V. I. Nat. Commun. 2013, 4, 2887). CuInZnS QDs are particularly attractive for fluorescent liquid penetrants because of their low toxicity, long term stability, large Stokes shift, bright luminescence, and broadband absorption spectra.

2. Overview

Full spectrum (visible to near-IR, 400-1300 nm) photoluminescent non-toxic fluorescent liquid penetrants are needed to identify surface discontinuities and to quantify their depths for manufactured parts for applications including, but not limited to, automobiles, aircraft, watercraft, bicycles, high-vacuum equipment, scientific equipment, spacecraft, robotics architecture, assembly lines and welding. Existing methods for identification and depth analysis for fluorescent liquid penetrants have not yet been envisioned, but are required in parallel.

Novel fluorescent liquid penetrants are disclosed herein which, in a preferred embodiment, contain non-carcinogenic QDs having tunable PL spectra with peaks in the visible (400-650 nm) to near-IR (650-1300 nm) and having a large Stokes shift so as to limit self-absorption of their own photoluminescence, which enables the characterization of the depth of surface discontinuities by analyzing the intensity and shape of the photoluminescence of the fluorescent liquid penetrant that has entered the said surface discontinuity. In some embodiments, multiple fluorescent liquid penetrants comprising different sizes and/or compositions of QD emitters would be used to accurately characterize the depth of the surface discontinuity. $CuInS_2$/ZnS QDs are a preferred, though non-limiting, photoluminescent material for this purpose.

Methods of surface discontinuity depth characterization are also disclosed which involve pulsed LED excitation and spectrally-resolved detection. The PL intensity may be characterized by a photodetecting camera which will be able to image the two-dimensional surface of the discontinuity and correlate that area with the PL intensity, and/or PL peak shift, to quantify the depth of the surface discontinuity.

The compositions, systems and methodologies disclosed herein represent an improvement over previous non-destructive testing methods that utilize liquid penetrants for identification of surface discontinuities in manufactured parts or welds. This is due, in part, to their ability to provide depth characterization, a feature not found in previously developed test methods of this type. Providing depth information of surface discontinuities is highly advantageous from a cost perspective, since it may limit the number of manufactured parts and/or welds that need to be removed or repaired, and that previously developed testing methods would not have avoided. The compositions, systems and methodologies disclosed herein may be utilized to provide a simple, safe, rapid, and cost-effective solution to surface discontinuity detection and characterization for manufactured parts and welds.

3. Definitions and Abbreviations

The following explanations of terms and abbreviations are provided to better describe the present disclosure and to guide those of ordinary skill in the art in the practice of the present disclosure.

Beer-Lambert Law: A law that relates the attenuation of light to the properties of the material through which the light is traveling. In particular, this law provides that the absorbance of a material sample is directly proportional to its thickness (path length), and that the absorbance is also proportional to the concentration of the absorbing species.

Carcinogen: A material that has been shown to directly or indirectly cause cancer in any mammal.

Emission spectrum: Those portions of the electromagnetic spectrum over which a fluorophore exhibits PL (in response to excitation by a light source) whose amplitude is at least 1% of the peak PL emission.

Fluorescent liquid penetrant: A liquid solution applied by drop casting, spraying, submersion, painting, or other marking methods that seeps into surface discontinuities and can identify the said surface discontinuity by fluorescing a bright light when excited with a light source.

Fluorophore: a material which absorbs a first spectrum of light and emits a second spectrum of light.

Linker: A chemical passivation attached to a surface with a terminating group that will chemically attach to a second terminating group that is passivating a second surface.

Liquid Penetrant Examination: A method wherein a liquid is applied to the surface of a manufactured part or weld, and wherein the liquid penetrates into surface discontinuities to help identify those discontinuities.

Non-destructive testing: A method used to analyze a manufactured part or weld for flaws without damaging the manufactured part or weld.

Photoluminescence (PL): The emission of light (electromagnetic radiation, photons) after the absorption of light. It is one form of luminescence (light emission) and is initiated by photoexcitation (excitation by photons).

Polymer: A large molecule, or macromolecule, composed of many repeated subunits. Polymers range from familiar synthetic plastics such as polystyrene or poly(methyl methacrylate) (PMMA), to natural biopolymers such as DNA and proteins that are fundamental to biological structure and function. Polymers, both natural and synthetic, are created via polymerization of many small molecules, known as monomers. Exemplary polymers include poly(methyl methacrylate) (PMMA), polystyrene, silicones, epoxy resins, and nail polish.

Quantum Dot (QD): A nanoscale particle that exhibits size-dependent electronic and optical properties due to quantum confinement. The quantum dots disclosed herein preferably have at least one dimension less than about 50 nanometers. The disclosed quantum dots may be colloidal quantum dots, i.e., quantum dots that may remain in suspension when dispersed in a liquid medium. Some of the quantum dots which may be utilized in the compositions, systems and methodologies described herein are made from a binary semiconductor material having a formula MX, where M is a metal and X typically is selected from sulfur, selenium, tellurium, nitrogen, phosphorus, arsenic, antimony or mixtures thereof. Exemplary binary quantum dots which may be utilized in the compositions, systems and methodologies described herein include CdS, CdSe, CdTe, PbS, PbSe, PbTe, ZnS, ZnSe, ZnTe, InP, InAs, $Cu_2S$, and $In_2S_3$. Other quantum dots which may be utilized in the compositions, systems and methodologies described herein are ternary, quaternary, and/or alloyed quantum dots including, but not limited to, ZnSSe, ZnSeTe, ZnSTe, CdSSe, CdSeTe, HgSSe, HgSeTe, HgSTe, ZnCdS, ZnCdSe, ZnCdTe, ZnHgS, ZnHgSe, ZnHgTe, CdHgS, CdHgSe, CdHgTe, ZnCdSSe, ZnHgSSe, ZnCdSeTe, ZnHgSeTe, CdHgSSe, CdHgSeTe, $CuInS_2$, $CuInSe_2$, $CuInGaSe_2$, $CuInZnS_2$, $CuZnSnSe_2$, $CuIn(Se,S)_2$, $CuInZn(Se,S)_2$, and $AgIn(Se,S)_2$ quantum dots, although the use of non-toxic quantum dots is preferred. Embodiments of the disclosed quantum dots may be of a single material, or may comprise an inner core and an outer shell (e.g., a thin outer shell/layer formed by any suitable method, such as cation exchange). The quantum dots may further include a plurality of ligands bound to the quantum dot surface.

Quantum Yield (QY): The ratio of the number of emitted photons to the number of absorbed photons for a fluorophore.

Self-absorption: The reduction of intensity of emitted light from a plurality of fluorophores as the light travels through the same plurality of fluorophores. In many cases, self-absorption may be caused by a small Stokes shift or by overlap between the absorption and emission spectra of a fluorophore; however, the compositions, methodologies and apparatuses disclosed herein are not specifically limited to a particular cause of self-absorption.

Stokes shift: the difference in energy between the positions of the lowest energy absorption shoulder or local absorption maximum and the maximum of the emission spectrum.

Surface discontinuity: An unwanted flaw in a manufactured part or weld which includes, but is not limited to, cracks, pits, corrosion, holes, stress marks, and abrasions.

Toxic: Denotes a material that can damage living organisms due to the presence of phosphorus or heavy metals such as cadmium, lead, or mercury.

4. Best Mode

Figure 4:
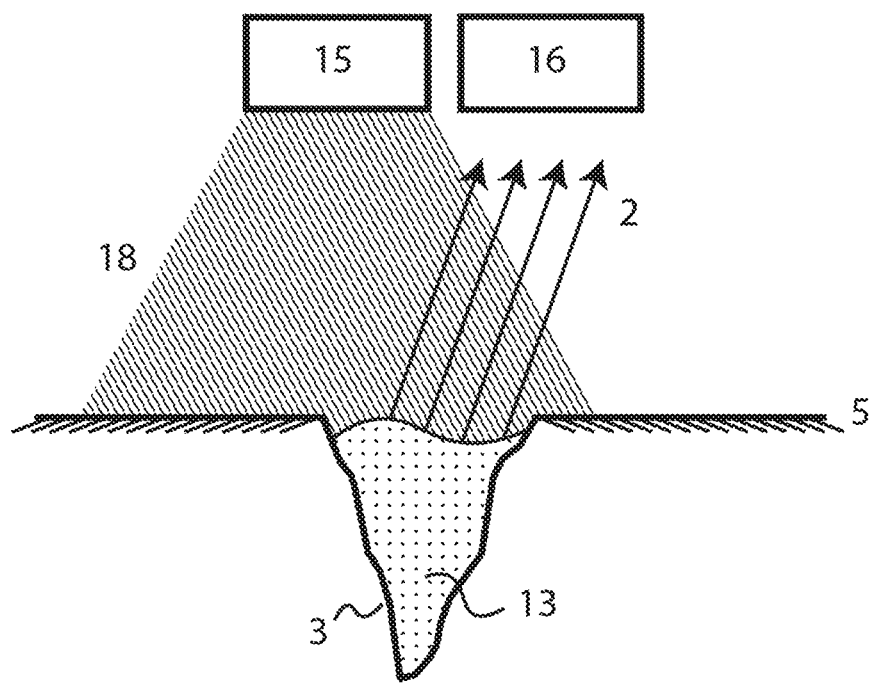
FIG. 4 is a schematic illustration of a surface discontinuity depth quantification system wherein an observer excites the fluorescent liquid penetrant with a light source, and wherein the photoluminescence properties of said fluorescent liquid penetrant are subsequently measured by a photodetector.
Figure 5:
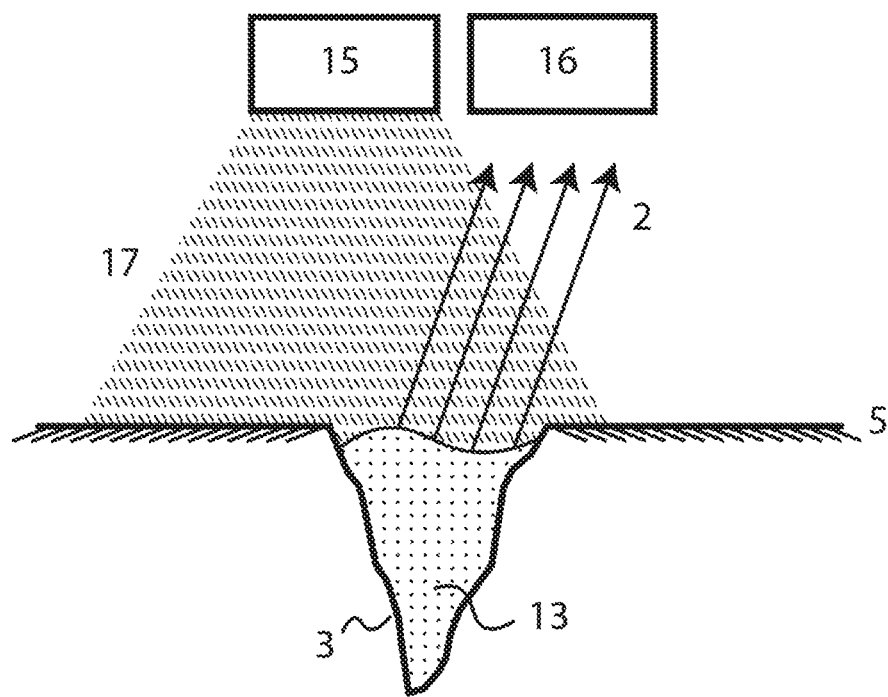
FIG. 5 is a schematic illustration of a surface discontinuity depth quantification system in which the fluorescent liquid penetrant is excited by a time-varying light source (such as, for example, a blue or UV LED), and wherein the time-varying photoluminescence is subsequently measured by a photodetector.

The preferred embodiment of the systems and methodologies disclosed herein includes the use of a fluorescent liquid penetrant comprising a mixture of one or more sizes and/or compositions of $CuInS_2$/ZnS QDs (see FIG. 2) and the spatially- and spectrally-resolved detection of the photoluminescence spectrum of the fluorescent liquid penetrant with one or more photodetectors (see FIGS. 4-5). FIG. 5 depicts the mode with the best defect detection and depth quantification, wherein light source 15b (which may be, for example, a blue or UV LED) emits a time-varying excitation 17 upon a fluorescent liquid penetrant containing QDs 13 that has been applied to a surface 5 and that has penetrated into a surface discontinuity 3 (this may be compared and contrasted to light source 15a in FIG. 4, which emits excitation 18 that may not be time-varying). The time-varying photoluminescence 2 from the fluorescent liquid penetrant 13 is then measured by the photodetector 16 (which may be, for example, a camera). The surface discontinuity 3 is detected, and the depth of the surface discontinuity is determined.

For example, in some embodiments of the device in FIG. 5, the time-varying light source 15b may excite the fluorescent liquid penetrant 13, thereby causing the fluorescent liquid penetrant to emit an emission spectrum. The integrated intensity and peak shift of the emission spectrum, as well as the luminescent area of the fluorescent liquid penetrant, are measured by the photodetector and processed by an electrical component (which may be, for example, a smartphone) to determine the depth of the surface discontinuity 3.

Figure 7:
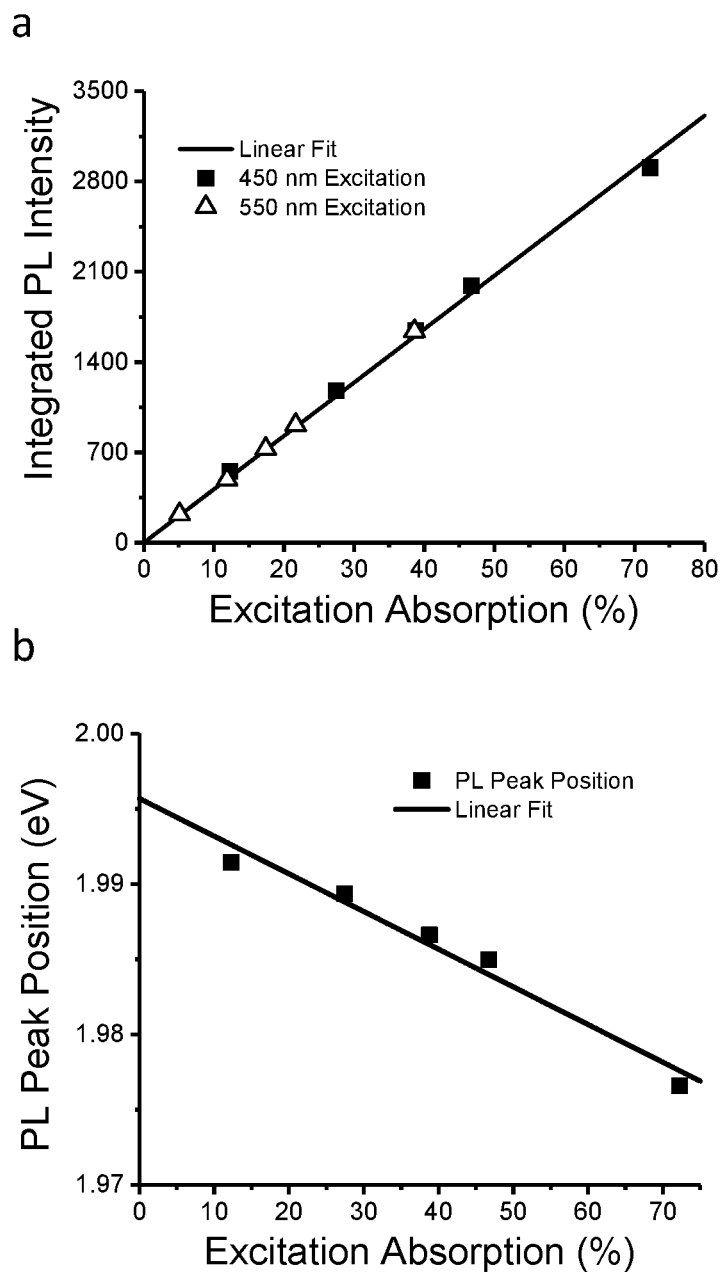
FIG. 7 is a series of graphs illustrating the principle of depth detection of a surface discontinuity by showing the photoluminescence spectra of an exemplary CuInZnS QD suspended in toluene in a 1 cm cuvette for various QD concentrations. Panel (a) shows the integrated PL of the QDs as a function of 450 nm excitation light absorbed in the 1 cm path length, as the concentration of the sample is varied. The data is easily modeled with a linear fit, thus confirming the low self-absorption of the QDs, even when ~75% of the excitation light is absorbed in a 1 cm path length. Panel (b) shows a small linear peak shift to lower emission energies as the concentration of QDs is increased.

Depending on the range of depth detectability needed for a given application, the concentration of the fluorescent liquid penetrant containing $CuInS_2$/ZnS QDs can be varied. As seen in FIG. 7, these QDs show a linear trend between the integrated PL spectrum and excitation absorption up to at least 75% in a 1 cm cuvette (OD=0.6). Since most surface discontinuities will be less than 1 cm, the concentration of QDs in the fluorescent liquid penetrant can be linearly increased by the inverse of the path length. For example, in the solution of QDs corresponding to the graphs of FIG. 7, where the path length for the sample was 1 cm, if defects were expected to be 1 mm or less, then according to the Beer-Lambert law, the concentration of QDs in the fluorescent liquid penetrant could be increased ten-fold, while still maintaining the linear relationship between integrated PL intensity and depth. By using a higher concentration of QDs for smaller surface discontinuity depths, the overall PL intensity can remain at sufficiently bright levels to be measured by the photodetector.

Additional depth resolution may be achieved by using two or more different fluorescent liquid penetrants that are comprised of different QD sizes and/or compositions so in that the PL emission of the two fluorescent liquid penetrants are different colors. By confirming the depth of the defect using multiple colors, a statistical error can be determined.

5. Making and Using the Best Mode

In the best mode of the system depicted in FIG. 5, QDs may be added to an existing liquid medium commonly used for liquid penetrants. The fluorescent liquid penetrant containing QDs may then be applied to a surface of a manufactured part or weld by any suitable method of deposition including, but not limited to, aerosol spraying, brush painting, airless spraying, wiping, dipping, or other suitable application methods as are known to the art. Excess fluorescent liquid penetrant is then wiped from the part, leaving only surface discontinuities with the penetrant remaining. The detector utilized in this methodology is preferably a compact and handheld device which preferably includes a pulsed UV LED, photodetectors, camera imaging system, at least one microcontroller, and other necessary electronics (such as, for example, a lock-in amplifier). Such devices are commercially available, and may be manufactured using techniques that are well known in the consumer electronics industry.

Figure 3:
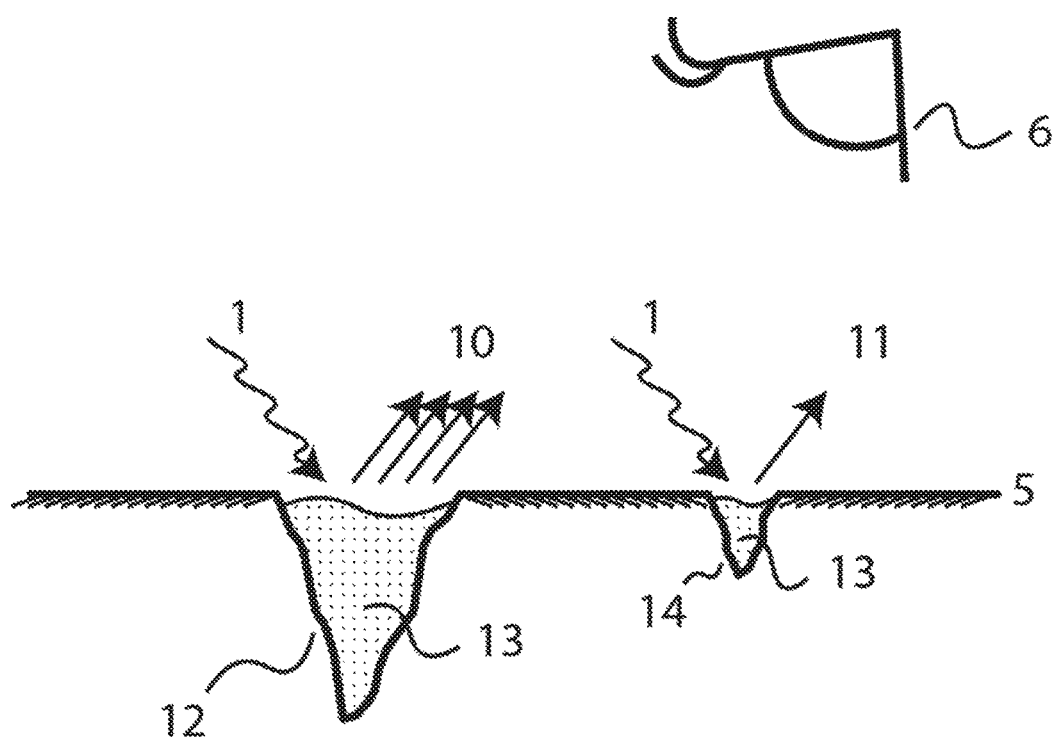
FIG. 3 is a schematic illustration of a fluorescent liquid penetrant with low self-absorption applied to a deep and shallow surface discontinuity wherein the observer is able to quantify the depth of the surface discontinuity by the photoluminescence intensity emanating from the fluorescent liquid penetrant.

For a quick identification mode, shown in FIGS. 1 and 3, the fluorescent liquid penetrant is excited by a handheld light source (such as, for example, a UV LED flashlight), and the resulting photoluminescence is observed visually. This approach provides a simple, low-tech, first detection, as desired. In this mode, the observer will be able to visually detect various magnitudes of defect depths by the brightness of the luminescence.

For further characterization of the depths of the surface discontinuities, the handheld device may be used to image the surface area of the defect, as well as the photoluminescence properties, in order to determine the depth of the defect being characterized. Preferably, in this mode, the excitation source is pulsed, and the resulting pulsed luminescence is measured by a photodetector using lock-in detection, so as to eliminate any false readings from ambient light.

For applications in which applicable specifications requires that defects of a certain depth be repaired, the handheld device may be equipped with at least first and second light sources which may be utilized to determine whether a surface defect passes the depth criteria. For example, the handheld device may be equipped with a red and green light that indicate if the surface defect passes the depth criteria (green light) or fails the depth criteria (red light). The tolerances may be tunable so the same handheld device may be used for various testing applications, which may require different regulations on the depth of the surface defect.

After inspection of all surface discontinuities is completed, the fluorescent liquid penetrant may be readily removed using a cleaning liquid that dissolves the penetrant. This may be accomplished by spraying the cleaning solution on the tested surface, or by simply submersing the part in a bath of the cleaning solution. Parts and/or welds that pass inspection may then still be used for their intended application, while parts that fail the inspection may be repaired or discarded.

6. Examples

The following examples are non-limiting, and are merely intended to further illustrate the compositions, systems and methodologies disclosed herein.

Example 1

This example illustrates that colloidal QDs composed of $CuInS_2/ZnS$ can be effective fluorophores for LPE.

Figure 6:
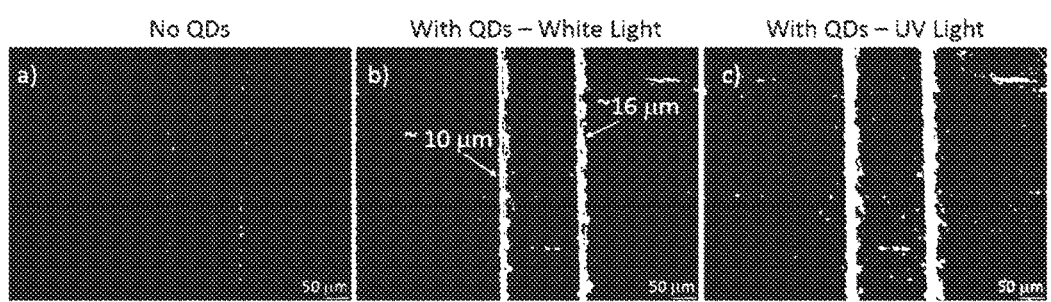
FIG. 6 shows indentions in metal that were stamped by a razor blade. Panel (a) shows the sample with multiple indentions, before being coated with $CuInS_2$ QD solution. Panel (b) shows the same indentions, under white light illumination, after applying the QDs and removing excess dots from the surface. Panel (c) shows yellow luminescence from QDs that remain in the indentions after excitation with a UV light source.

As a test of this mode, different QD liquid penetrants were applied to test samples. Standard test samples were made from strips of steel with fabricated cracks of various lengths, widths and depths. These troughs provide ideal testing conditions for evaluating the ability of QD solutions to penetrate into different size cracks and to distinguish the cracks from the steel surface. The troughs were created by stamping the steel samples with a sharp object and a hammer, such as a razor blade (for parallel troughs), a nail (to simulate round pits) or wire mesh (to produce a grid of impressions). Varying the force of the hammer impact produces different widths and depths of the indentions as the sharp object presses further into the steel. The steel samples used were thin (0.008 in thick) tin-coated steel sheet metal pieces cut into 1"+1" samples that fit into a small integrating sphere (K-petite, Horiba) which was connected to a Horiba Fluoromax 4 spectrometer. These indentions (see FIG. 6) were characterized using an optical microscope (Olympus BX51) outfitted with multiple objectives ranging from 5× to 100× magnification. The width of each of the indentions was measured using the microscope's software.

Colloidal QD solutions are typically made by dispersing the QD powder into liquid solvents such as toluene. First and second samples of QDs were tested which had QYs of greater than 40% and greater than 90%, respectively. The use of low viscosity solvents in the colloidal solutions is beneficial in LPE applications, since they allow the solution to be highly penetrating. Solvent selection for the QD liquid penetrant is an important factor for both the application and cleaning steps of the testing procedure. In particular, the solvent must allow the QDs to completely penetrate and fill the small cracks in the steel samples, while also allowing the QDs to be removed from the undamaged steel surface but retained within the defects.

In light of the foregoing, experimental work was undertaken to determine which solvent, for a given size QD, yields the best penetration results for the widest range of surface crack dimensions. Toluene emerged from these tests as a preferred penetrant for some applications. However, one skilled in the art will appreciate that other media (such as, for example, inorganic solvents used in conjunction with low volatile organic compounds) may be preferred in some applications.

Experimental work was also undertaken to determine how QD concentration in the solvent affects the applicability of the penetrant to the test samples (see FIG. 7). Concentration determines the amount of solvent needed to create a highly penetrating fluorescent QD solution that is bright enough to detect small surface defects. However, the use of a solution having too low of a concentration of QDs may adversely affect the ability to detect surface flaws, since this may result in an insufficient amount of QD material deposited in the crack. In FIG. 7, concentrations of QDs in solution should not exceed 75% absorption of the excitation wavelength for 1 cm deep cracks. Since there is a linear relationship between absorption and concentration of the absorbing species, the concentration of the QDs in the fluorescent liquid penetrant can be inversely scaled as the dimensions of the biggest surface discontinuities is decreased. For example, if surface defects are expected to be 1 mm or less, the concentration could be increased by ten-fold and still demonstrate an accurate relationship between integrated PL intensity, and/or PL peak position, and defect depth.

Example 2

This example illustrates the use of the QD fluorescent liquid penetrant as an indicator of surface defects for different test material compositions and colors.

As seen in FIG. 1, a QD fluorescent liquid penetrant 4 is applied to a surface 5 of a manufactured part or weld that contains a surface discontinuity 3. After cleaning the surface of the manufactured part or weld, a UV light source 1 is used to excite the QD fluorescent liquid penetrant. The penetrant brightly luminesces 2, thus causing the surface discontinuity to be easily visible to an observer 6.

In this example, the PL color of the QD fluorescent liquid penetrant is carefully chosen to provide a stark contrast with the surface of the manufactured part or weld. Since QDs have a broad absorption spectrum (see FIG. 2, 7), the same excitation source can be used to excite the different colored PL emission from different fluorescent liquid penetrants.

In FIG. 3, a schematic is shown where an observer 6 is able to decipher the different depth magnitudes for two different surface discontinuities 12 and 14 by observing less intense PL 11 from the shallow surface discontinuity 14 since less QD fluorescent liquid penetrant 13 remains in the defect. For the deeper surface discontinuity 12, a more intense PL 10 is seen by the observer.

Example 4

This example illustrates the use of an NIR QD fluorescent liquid penetrant with peak emissions at 700 nm, 800 nm, 900 nm, 1000 nm, 1100 nm, and 1200 nm. These QDs are disposed in a liquid medium and can have QYs greater than 40% or greater than 90%.

These NIR QDs are effective liquid penetrants because NIR light does not scatter as easily, and therefore provides an effective fluorophore for LPE. These NIR were synthesized with core compositions of $CuInS_2$, $CuInSe_2$ and alloys thereof. In order to improve stability and to achieve QYs greater than 40%, a shell of ZnS or ZnSe was grown around the cores.

Example 5

This example illustrates the use of a QD fluorescent liquid penetrant and measurement apparatus to determine the depth of a surface discontinuity by measuring the photoluminescence peak position shift of the QD fluorescent liquid penetrant.

In panel (b) of FIG. 7, a linear relationship was observed between the PL peak position and percent absorption of a 450 nm excitation source for QDs suspended in a toluene solution contained within a 1 cm cuvette. The small shift in peak position is due to the small (but non-zero) overlap between the absorption 7 and PL emission 9 of the QDs seen in FIG. 2. This overlap causes a reduction in the higher photon energies of the PL spectrum as the concentration or path length of the QD solution is varied.

7. Additional Comments

Various modifications, substitutions, combinations, and ranges of parameters may be made or utilized in the compositions, devices and methodologies described herein without departing from the scope of the present disclosure.

For example, various fluorophores may be utilized in the compositions, methodologies and apparatuses disclosed herein. Preferably, the fluorescent liquid penetrant based on these fluorophores exhibits a photoluminescence maximum and absorption onset having a wavelength separation that is characterized by a Stokes shift of more than 200 meV, more preferably by more than 300 meV, and most preferably by more than 400 meV. Preferably, the fluorescent liquid penetrant has a photoluminescence quantum yield of greater than 40%, more preferably greater than 60%, even more preferably greater than 80%, and most preferably greater than 90%.

One skilled in the art will also appreciate that fluorescent liquid penetrants may be produced in accordance with the teachings herein that exhibit self-absorption across various regions of the spectrum. The properties of these penetrants may be selected or tailored for specific applications. Thus, for example, fluorescent liquid penetrants may be produced in accordance with the teachings herein which exhibit a targeted self-absorption over a targeted region of the integrated spectrum. For example, the targeted self-absorption may be less than 90%, preferably less than 75%, more preferably less than 60%, and most preferably less than 50% over the targeted region of the integrated spectrum. The targeted region of the integrated spectrum may vary from one application to another, but is typically the portion of the integrated spectrum over distances of 100 nm to 10 cm, though in some applications the targeted region of the integrated spectrum may be 100 nm to 10000 nm or 1000 nm to 10000 nm. In a particularly preferred embodiment, the fluorescent liquid penetrant exhibits a self-absorption of less than 50% across the integrated spectrum over distances of 1 um to 1 cm.

The fluorescent liquid penetrants disclosed herein may have photoluminescence which is characterized by light emission having wavelengths within a specified range. Typically, this specified range is 300 nm to 1300 nm, preferably 400 nm to 1000 nm, more preferably 500 nm to 900 nm, and most preferably 540 nm to 850 nm.

The fluorescent liquid penetrants disclosed herein may have photoluminescence which is characterized or described in various ways without departing from then scope of the present disclosure. For example, in some cases, the photoluminescence may be described in terms of the amount it drops with respect to its initial or shallow value. By way of example, in such a case, if the liquid penetrant is described as having a (e.g., targeted) self-absorption of less than 90%, this would mean that the photoluminescence drops to 10% of its initial/shallow value.

As used herein, "comprising" means "including" and the singular forms "a" or "an" or "the" include plural references unless the context clearly indicates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure relates. Suitable methods and compositions are described herein for the practice or testing of the compositions, systems and methodologies described herein. However, it is to be understood that other methods and materials similar or equivalent to those described herein may be used in the practice or testing of these compositions, systems and methodologies. Consequently, the compositions, materials, methods, and examples disclosed herein are illustrative only, and are not intended to be limiting. Other features of the disclosure will be apparent to those skilled in the art from the following detailed description and the appended claims. Unless otherwise indicated in the disclosure, one skilled in the art will appreciate that the various features described in the appended claims may be combined in various ways without departing from the scope of the present application.

Unless otherwise indicated, and with respect to all numbers expressing quantities of components, percentages, temperatures, times, and so forth, the scope of the present disclosure includes all instances of such numbers as if modified by the term "about." Similarly, unless otherwise indicated, and with respect to all non-numerical properties, the scope of the present disclosure includes all instances of such non-numerical properties as if modified by the term "substantially", which term shall mean "to a great extent or degree". Moreover, unless otherwise indicated implicitly or explicitly, the numerical parameters and/or non-numerical properties set forth are approximations that may depend on the desired properties sought, the limits of detection under standard test conditions or methods, the limitations of the processing methods, and/or the nature of the parameter or property. When directly and explicitly distinguishing embodiments from discussed prior art, the embodiment numbers are not approximations unless the word "about" is recited.

What is claimed is:

1. A fluorescent liquid penetrant, comprising:
a liquid medium; and
first and second fluorophores disposed in said medium;
wherein said first and second fluorophores have first and second distinct emissions spectra associated with them,
wherein said first and second fluorophores are selected from the group consisting of nanocrystals and quantum dots, and wherein said fluorescent liquid penetrant has a photoluminescence quantum yield that is greater than 40% and that exhibits a self-absorption of less than 50% across the integrated spectrum over distances of 100 nm to 10 cm.

2. The fluorescent liquid penetrant of claim 1, wherein said fluorescent liquid penetrant has a photoluminescence quantum yield that is greater than 90%.

3. The fluorescent liquid penetrant of claim 1, wherein said first and second fluorophores comprise quantum dots, wherein said quantum dots comprise a semiconductor material, and wherein said quantum dots do not contain any element selected from the group consisting of phosphorus, lead, cadmium, and mercury.

4. The fluorescent liquid penetrant of claim 1, wherein said first and second fluorophores comprise quantum dots, and wherein said plurality of quantum dots comprise at least one material selected from the group consisting of $CuInS_2$, $CuInSe_2$, $AgInS_2$, $AgInSe_2$, $CuGaS_2$, $CuGaSe_2$, $AgGaS_2$, $AgGaSe_2$, $CuInGaS_2$, $CuInGaSe_2$, ZnS, and ZnSe.

5. The fluorescent liquid penetrant of claim 1, wherein said first and second fluorophores comprise quantum dots, wherein said quantum dots comprise a core/shell structure, and wherein the shell material is selected from the group consisting of metal sulfides, metal selenides, metal oxides, and carbon-based materials.

6. The fluorescent liquid penetrant of claim 1, wherein said liquid medium contains a polymer.

7. The fluorescent liquid penetrant of claim 1, wherein said fluorescent liquid penetrant exhibits a photoluminescence which is characterized by light emission having wavelengths in the range of 400 nm to 1300 nm.

8. The fluorescent liquid penetrant of claim 1, wherein said fluorescent liquid penetrant exhibits a photoluminescence maximum and absorption onset having a wavelength separation that is characterized by a Stokes shift of more than 200 meV.

9. The fluorescent liquid penetrant of claim 1, wherein each of said first and second fluorophores comprises a linker binding the fluorophore to the surface discontinuity, and wherein the linker comprises a first functional group that binds to the said plurality of fluorophores and a plurality of second functional groups that bind to surface discontinuities.

10. In combination with the fluorescent liquid penetrant of claim 1, an optical apparatus for analyzing surface discontinuities with said fluorescent liquid penetrant, the apparatus comprising:
a light source which excites said fluorescent liquid penetrant;
at least one photodetector which analyzes the intensity or peak shift of said photoluminescence; and
an electronics module which determines the depth of the surface discontinuity by monitoring the intensity or peak shift of said photoluminescence with said at least one photodetector.

11. The combination of claim 10, wherein said light source is selected from the group consisting of LEDs, laser diodes, dye lasers, fiber lasers, and solid-state lasers.

12. The combination of claim 10, wherein said at least one photodetector comprises a material selected from the group consisting of silicon, germanium, cadmium sulfide, indium phosphide, copper indium diselenide, indium gallium arsenide and gallium arsenide.

13. The combination of claim 10, further comprising a microcontroller in electrical communication with said light source and said at least one photodetector, wherein said microcontroller characterizes the depth of said surface discontinuity by monitoring the intensity or peak shift of said photoluminescence with lock-in detection.

14. The method of claim 13, wherein the at least one surface discontinuity is in a weld.

15. The fluorescent liquid penetrant of claim 1, wherein said first and second fluorophores have first and second distinct absorption spectra associated with them.

16. A method of non-destructively measuring the depth of at least one surface discontinuity on the surface of a substrate, comprising:
applying at least one fluorescent liquid penetrant to the surface, thereby forming a treated surface, wherein said at least one fluorescent liquid penetrant contains first and second fluorophores having first and second distinct emissions spectra associated with them and is characterized by a photoluminescence self-absorption of less than 50% across the integrated spectrum, and wherein said first and second fluorophores are selected from the group consisting of nanocrystals and quantum dots;
illuminating said treated surface with light from a light source, thereby causing said at least one fluorescent liquid penetrant to produce photoluminescent light; and
measuring the intensity and peak shift of the said photoluminescent light with an optical apparatus.

17. The method of claim 16, wherein the at least one liquid penetrant includes first and second fluorescent penetrants, and further comprising:
using the photoluminescent light of the first and second fluorescent penetrants that produce photoluminescent light of first and second distinct colors when illuminated by said light source to quantify the depth of said at least one surface discontinuity.

18. The method of claim 16, wherein said first and second fluorophores comprise a material selected from the group consisting of doped nanocrystals, thick shell core/shell quantum dots, quantum dots with intrinsic Stokes shift greater than 100 meV.

19. The method of claim 16, wherein said photoluminescence is absorbed by less than 50% across the integrated spectrum by said fluorescent penetrant over distances of 100 nm to 10 cm.

20. The method of claim 16, wherein the at least one surface discontinuity is on a manufactured part selected from the group consisting of automotive parts, aircraft parts, submarine parts, weapons, scientific equipment parts, high-vacuum parts, ship parts, spacecraft parts, bicycle parts, robot parts, architectural parts, and assembly line parts.

21. The method of claim 16, wherein said optical apparatus comprises a camera coupled with image processing software.

* * * * *